(12) United States Patent
Koripelly et al.

(10) Patent No.: US 11,465,945 B2
(45) Date of Patent: Oct. 11, 2022

(54) UREA CONDENSATION COMPOSITIONS AND METHODS OF MAKING THE SAME

(71) Applicant: SABIC GLOBAL TECHNOLOGIES B.V., Bergen Op Zoom (NL)

(72) Inventors: Rajamalleswaramma Koripelly, Bangalore (IN); Radha Achanath, Bangalore (IN); Chandra Mohana, Bangalore (IN); Samik Gupta, Bangalore (IN)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 112 days.

(21) Appl. No.: 16/606,968

(22) PCT Filed: Apr. 16, 2018

(86) PCT No.: PCT/IB2018/052635
§ 371 (c)(1),
(2) Date: Oct. 21, 2019

(87) PCT Pub. No.: WO2018/197991
PCT Pub. Date: Nov. 1, 2018

(65) Prior Publication Data
US 2020/0048154 A1     Feb. 13, 2020

Related U.S. Application Data

(60) Provisional application No. 62/488,987, filed on Apr. 24, 2017.

(51) Int. Cl.
*C05C 9/02*     (2006.01)
*C08G 12/12*    (2006.01)

(52) U.S. Cl.
CPC ............. *C05C 9/02* (2013.01); *C08G 12/12* (2013.01)

(58) Field of Classification Search
CPC ...... C05C 9/02; C08G 12/12; C07C 273/1863
See application file for complete search history.

(56) References Cited

U.S. PATENT DOCUMENTS

| 3,322,528 A | 5/1967 | Hamamoto |
| 3,326,665 A | 6/1967 | Schafer et al. |
| 3,441,539 A | 4/1969 | Schafer et al. |
| 3,459,528 A | 8/1969 | Wiesboeck et al. |
| 3,585,019 A | 6/1971 | Hays |
| 3,870,755 A | 3/1975 | Kamo et al. |

(Continued)

FOREIGN PATENT DOCUMENTS

| CN | 1194633 A | 9/1998 |
| CN | 1196339 A | 10/1998 |

(Continued)

OTHER PUBLICATIONS

McVey, GR. "Methylene Urea—A Controlled Release Nitrogen Source for Turfgrass" 0. M. Scott & Sons Company pp. 60-72 (1979) (Year: 1979).*

(Continued)

*Primary Examiner* — Jennifer A Smith
(74) *Attorney, Agent, or Firm* — Norton Rose Fulbright US LLP

(57) ABSTRACT

Urea-aldehyde condensation compositions, processes for preparing the same, and the use of said compositions are disclosed. The compositions can have a nitrogen content that is 100% water soluble and can be used as a fertilizer.

10 Claims, 4 Drawing Sheets

(56) References Cited

U.S. PATENT DOCUMENTS

| | | | |
|---|---|---|---|
| 3,962,329 A | 6/1976 | Schoenaich et al. | |
| 3,961,329 A | 7/1976 | Naidich | |
| 4,062,890 A | 12/1977 | Shank | |
| 4,089,899 A * | 5/1978 | Greidinger | C05C 9/02 564/59 |
| 4,102,840 A | 7/1978 | Pusch | |
| 4,243,797 A | 1/1981 | Peterson et al. | |
| 4,298,512 A | 11/1981 | Sartoretto et al. | |
| 4,411,683 A | 10/1983 | Goertz | |
| 4,599,102 A | 7/1986 | Hawkins | |
| 5,039,328 A | 8/1991 | Saitoh et al. | |
| 5,124,451 A | 7/1992 | Hackl et al. | |
| 5,169,954 A | 12/1992 | Hackl et al. | |
| 5,414,083 A | 5/1995 | Hackl et al. | |
| 5,597,917 A | 1/1997 | Hackl et al. | |
| 6,306,194 B1 * | 10/2001 | Wertz | C05G 5/20 71/30 |
| 7,468,087 B2 | 12/2008 | Sakamoto et al. | |
| 9,340,495 B2 | 5/2016 | Hashmi et al. | |
| 2003/0154754 A1 | 8/2003 | Costa et al. | |
| 2009/0165515 A1 | 7/2009 | Hiroshi et al. | |
| 2014/0047884 A1 | 2/2014 | Gabrielson et al. | |
| 2015/0101379 A1 | 4/2015 | Gabrielson et al. | |
| 2016/0060182 A1 | 3/2016 | Cook | |
| 2016/0340265 A1 | 11/2016 | Kanagalingam et al. | |

FOREIGN PATENT DOCUMENTS

| | | |
|---|---|---|
| CN | 101041593 | 9/2007 |
| CN | 101759481 | 6/2010 |
| CN | 103011982 | 4/2013 |
| CN | 104812723 | 7/2018 |
| DE | 1146080 | 3/1963 |
| DE | 1543201 | 6/1970 |
| DE | 1905834 | 11/1972 |
| DE | 142044 | 6/1980 |
| DE | 4128828 | 3/1993 |
| DE | 19631764 | 2/1998 |
| EP | 0877722 | 11/1998 |
| EP | 1170272 | 1/2002 |
| EP | 1174402 | 1/2002 |
| EP | 1288179 | 3/2003 |
| EP | 1724247 | 11/2006 |
| GB | 949408 | 2/1964 |
| GB | 1099643 | 1/1968 |
| GB | 1212605 | 11/1970 |
| WO | WO 2014/016745 | 1/2014 |
| WO | WO 2015/114542 | 8/2015 |
| WO | WO 2017/013573 | 1/2017 |

OTHER PUBLICATIONS

Ando, et al., "Plant Nutrition For Sustainable Food Production and Environment," *Proceedings of the XIII International Plant Nutrition Colloquium*, 1997, 13-19:639-640.

Bose, et al., "New protocol for Biginelli reaction—a practical synthesis of Monastrol," *ARKIVOC*, 2005, 3:228-236.

European Search Report for Application No. 12005353.3, dated Nov. 28, 2012.

Gautney, et al., "Feasibility of cogranulating the nitrogen loss inhibitors dicyandiamide, thiourea, phenyl phosphorodiamidate, and potassium ethyl xanthate with urea," *Ind. Eng. Chem. Prod. Res. Dev.*, 1984, 23:483-489.

International Search Report and Written Opinion issued in International Patent Application No. PCT/IB2018/052635, dated Jul. 9, 2018.

International Search Report issued in International Patent Application No. PCT/IB2013/055928, dated Oct. 28, 2013.

Jahns, et al., "Biodegradability of Urea-Aldehyde Condensation Products," *Journal of Polymers and the Environment*, 2003, 11(4):155-159.

Lunt, et al., "Properties and Value of 1,1-Diureido Isobutane (IBDU) as a Long-Lasting Nitrogen Fertilizer," *J. Agr. Food Chem.*, 1969, 17(6):1269-1271.

Mobinikhaledi et al., Synthesis of some 2-oxo and 2-thioxo substituted pyrimidines using solvent-free conditions, *Journal of Heterocyclic Chemistry*, 2007, 44:697-699.

Office Action issued in corresponding Australian Patent Application No. 2013294659, dated Jun. 10, 2015.

Office Action issued in corresponding Chinese Patent Application No. 201380039066.5, dated Sep. 17, 2015. (Machine Translation Provided).

Office Action issued in corresponding Indian Application No. 10324/DELNP/2014, dated Jan. 15, 2018.

Office Action issued in corresponding Taiwanese Application No. 102126107, dated Jul. 15, 2016.

Reddy, et al., New environmentally friendly solvent free synthesis of dihydropyrimidinones catalysed by N-butyl-N, N-dimethylphenylethylammonium bromide, *Tetrahedron Letters*, 2003, 44:8173-8175.

Wirtz, et al., "Ethanolamines and Propanolamines to Fiber, 4 Synthetic Organic;" *Ullmann's Encyclopedia of Industrial Chemistry*, 1987; 5, (10):363-401.

Watson, et al., "Rate and mode of application of the urease inhibitor N-(n-butyl) thiophosphoric triamide on ammonia volatilization from surface-applied urea," *Soil Use and Management*, 2008, 24:246-253.

International Search Report and Written Opinion issued in International Patent Application No. PCT/IB2019/000869, dated Jan. 8, 2020.

Office Action Search Report issued in corresponding Chinese Patent Application No. 201880034214.7, dated Nov. 23, 2021.

* cited by examiner

UREA CONDENSATION COMPOSITIONS AND METHODS OF MAKING THE SAME

CROSS REFERENCE TO RELATED APPLICATIONS

This application is a national phase application under 35 U.S.C. § 371 of International Application No. PCT/IB2018/052635, filed Apr. 16, 2018, which claims the benefit of priority of U.S. Provisional Patent Application No. 62/488,987 filed Apr. 24, 2017, which are hereby incorporated by reference in their entirety.

BACKGROUND OF THE INVENTION

A. Field of the Invention

The invention generally concerns urea-aldehyde condensation compositions, processes for preparing the same, and the use of the condensation compositions as fertilizers. The condensation compositions can be free of hot water insoluble nitrogen (HWIN).

B. Description of Related Art

Urea-aldehyde condensates and polymers thereof are typically used in products ranging from slow-release fertilizers and feed for cattle to binders, resins, plastics, and insulating materials (Jahns et al. Journal of Polymers and the Environment (2003) 11:155; U.S. Pat. No. 9,340,495). Short chain urea-aldehyde condensates and polymers are especially valuable for use in fertilizers because of their water soluble nitrogen content.

Conventionally, urea-aldehyde condensates are generated by the reaction of urea with formaldehyde and optionally a higher aldehyde (C2 and greater aldehyde) under acidic conditions and temperatures of greater than 50° C. to form urea-aldehyde condensate polymers (see U.S. Pat. Nos. 3,459,528; 4,298,512). The reaction is typically stopped by increasing the pH to approximately 7 to 8. When a higher aldehyde is used, molar ratios of formaldehyde to higher aldehyde are typically 9:1 to 1:3.

However, synthesis of short chain urea condensed products can be challenging due to the rate of polymerization. In particular, the ratio of urea to aldehyde(s) or amides, reaction temperatures, and the order of addition of the reactants can play a major role in the degree of polymerization, which can detrimentally affect the water soluble content of the resulting reaction products. As an example, U.S. Pat. Nos. 3,441,539 and 4,298,512 each disclose the use of various reaction conditions to form urea condensates. These condensates included HWIN or insoluble nitrogen when isobutyraldehyde, isobutylidenediurea (IBDU), or acetaldehyde were used in the condensation reaction.

The presence of HWIN in short chain urea-aldehyde condensate fertilizer products can result in a product that does not provide a consistent and steady release of nitrogen to plants throughout a given growing season. For example, HWIN can be undesirable in quick release fertilizers. Further, the slow nature of nitrogen release from HWIN can result in irregular fertilization of plants and negatively affect plant growth and production.

SUMMARY OF THE INVENTION

A discovery has been made that provides a solution to the aforementioned problems associated with producing urea-aldehyde condensate products. In particular, the solution is premised on reacting urea with various C1-C4 aldehydes under particular reaction conditions to form urea-aldehyde condensates that can be free of HWIN. In preferred instances, the reactants can include urea, a first C1-C4 aldehyde (e.g., formaldehyde, butyraldehyde, isobutyraldehyde, or crotonaldehyde), and at least a second C1-C4 aldehyde that can be the same or different than the first C1-C4 aldehyde. The reaction can be run at a temperature of 25° C. to up to 100° C. and the temperature can be the same or different in each step of the reaction. Additionally, the process can begin with a base-catalyzed reaction and then be pushed to an acid-catalyzed reaction (e.g., by adjusting the pH of the reaction medium from basic to acidic). Notably, the C1-C4 aldehydes can be introduced at different periods of time (e.g., a first C1-C4 aldehyde can be introduced during the base-catalyzed reaction and additional C1-C4 aldehydes can also be introduced during the base-catalyzed reaction and/or during the acid-catalyzed reaction). Without wishing to be bound by theory, it is believed that apart from reaction conditions such as temperature and time, the order of addition of reactants allows for more efficient control of the degree of polymerization during the reaction and can result in urea-aldehyde condensates free of HWIN. Also, the inclusion of a second C1-C4 aldehyde during the acidification step is believed to provide the ability to control the amount of cold water soluble nitrogen (CWSN) and hot water soluble nitrogen (HWSN) present in the resulting product. Still further, the process of the present invention can be performed in a single reaction chamber or vessel (i.e., a "one-pot" reaction scheme) by adjusting the pH of the reaction mixture from basic to acidic and then to neutral to stop the reaction, which provides for an efficient and scalable production process that can meet the ever growing needs of the fertilizer industry.

In one aspect of the present invention, a method for producing a urea condensation composition is disclosed. The method can include (a) reacting a solution containing urea, formaldehyde, and at least one C2-C4 aldehyde under basic conditions to form a first composition, and (b) acidifying the first composition to form a urea condensation composition containing at least one urea oligomer. Alternatively, the method can include (a) reacting a solution containing urea and formaldehyde under basic conditions to form a first composition, and (b) reacting the first composition and at least one C2-C4 aldehyde under acidic conditions to form a urea condensation composition containing at least one urea oligomer. Still further, the method can include (a) reacting a solution containing urea and at least one first C1-C4 aldehyde or a derivative thereof under basic conditions to form a first composition, and (b) reacting the first composition and at least one second C1-C4 aldehyde or a derivative thereof under acidic conditions to form a urea condensation composition containing at least one urea oligomer. In preferred instances, the first and second C1-C4 aldehydes are different. In each alternative, the resulting urea condensation composition can be free of HWIN.

In some instances, step (a) includes heat-treating the solution at a temperature of 40° C. to up to or less than 100° C., 50° C. to up to or less than 70° C., 60° C., 50° C., or any range therein. The solution in step (a) can react for any amount of time. In some instances, the reaction is reacted for at least 30 minutes, for no more than 90 minutes, and/or for 60 minutes, or any time therein. In some instances, the solution in step (a) has a pH of about 8 to about 10.

The amount of the urea, formaldehyde, at least one C2-C4 aldehyde, and/or at least one C1-C4 aldehyde in the reaction step (a) can be any amount sufficient to carry out the base-catalyzed reaction. In some instances, the mol. % ratio of urea to the combined formaldehyde and the at least one C2-C4 aldehyde in step (a) is 2:1 or greater. In some instances, the mol. % ratio of formaldehyde to the at least one C2-C4 aldehyde is 9:1 to 1:3 in step (a). In some instances, the mol. % ratio of urea to the combined formaldehyde and the at least one C2-C4 aldehyde is 2:1 or greater, and the mol. % ratio of formaldehyde to the at least one C2-C4 aldehyde is 9:1 to 1:3 in step (a).

In some instances, the pH of the first composition in step (b) is decreased to about 2 to about 5. In some instances, step (b) polymerizes the urea in the presence of the one or more aldehyde. In some instances, the acidifying step (b) is performed at a temperature of 25° C. to up to or less than 60° C., and/or at 45° C., or any temperature therein. In some instances, the acidified step (b) can further include allowing the acidified composition to polymerize for any amount of time. In some instances, the acidified composition is allowed to polymerize for at least 30 minutes, for no more than 90 minutes, and/or for 60 minutes, or any time therein. In further instances, the pH of the reaction in step (b) can subsequently be increased to neutral (about 7 to about 8, preferably about 7 to 7.5) or a basic pH to stop the polymerization reaction.

The C1-C4 aldehydes used in the processes of the present invention can be any C1-C4 aldehyde, derivative thereof, or combination thereof. In some instances, the C1-C4 aldehydes can be formaldehyde, butyraldehyde, isobutyraldehyde, crotonaldehyde, or any combination thereof. The formaldehyde can be in a variety of forms such as its aldehyde form ($CH_2O$), its hydrated form (methanediol), and its paraformaldehyde form. In some particular instances, the formaldehyde can be urea formaldehyde concentrate-85, or formalin containing 37-65% formaldehyde.

The method of the present invention can produce urea oligomers. In some instances, the urea is condensed with formaldehyde, a C2-C4 aldehyde, a first C1-C4 aldehyde, a second C2-C4 aldehyde or any combination thereof. In some instances, the method produces more than one urea oligomer. In some instances, the method consumes 85 wt. % or more of the urea (product contains 15 wt. % or less urea). In some instances, the method produces at least one C1-C4/urea oligomer and consumes at least 85 wt. % of the urea. In some instances, the method produces at least one methylene urea oligomer and at least one isobutylidenediurea derivative. In some instances, the at least one C1-C4/urea oligomer includes isobutylidenediurea, mono (ureidomethylene) isobutylenediurea, bis(ureidomethylene) isobutylenediurea, and at least two, three, or all four methylene urea oligomers selected from the group consisting of methylene diurea, dimethylene triurea, trimethylene tetraurea, and tetramethylene pentaurea.

The methods of the present invention can be used to produce a urea condensation composition wherein 100% of the nitrogen content is water soluble. In some instances, the nitrogen content is at least 32%, 32% to 42%, or 35 to 38% by weight of the composition. In some instances, the water-soluble nitrogen content contains 50%, 50% or more, 60% or more, 75% or more, 80% or more, or 82% or more of cold water-soluble nitrogen content.

In some aspects of the present invention, there is disclosed a method for producing a urea condensation composition by (a) heat-treating a basic aqueous solution having a pH of about 8 to about 10 to a temperature of 40° C. to less than 100° C. for 30 minutes to 90 minutes, the basic aqueous solution containing urea, formaldehyde, and isobutyraldehyde, wherein the mol. % ratio of formaldehyde to isobutyraldehyde is 9:1 to 1:3 and the mol. % ratio of urea to the combined formaldehyde and isobutyraldehyde is 2:1 or greater, and (b) acidifying the basic aqueous solution from step (a) to have a pH of about 2 to about 5 to polymerize the urea in the presence of the formaldehyde and isobutyraldehyde at 25° C. to less than 60° C. for 30 minutes to 90 minutes, preferably at 45° C. for 60 minutes, to form a urea condensation composition containing at least one methylene urea oligomer and at least one isobutylidenediurea derivative.

Also disclosed in the context of the present invention is a urea-condensation composition containing at least one C1-C4/urea oligomer and includes less than 15 wt. % urea and has a nitrogen content that is 100% water-soluble (i.e., all of the nitrogen in the composition is water soluble). In some instances, the water-soluble nitrogen content is 50%, 50% or more, 60% or more, 75% or more, 80% or more, or 82% or more of cold water-soluble nitrogen. In some instances, the at least one C1-C4/urea oligomer includes at least one isobutylidenediurea derivative and at least one methylene urea oligomer. In some instances, the at least one C1-C4/urea oligomer includes isobutylidenediurea, mono (ureidomethylene) isobutylenediurea, bis(ureidomethylene) isobutylenediurea, and at least two, three, or all four methylene urea oligomers selected from the group consisting of methylene diurea, dimethylene triurea, trimethylene tetraurea, and tetramethylene pentaurea.

The urea condensation composition or one or more chemicals therein can be formulated into any composition, such as, but not limited to, fertilizers, edible products, binders, resins, plastics, and insulating materials. In some instances, the composition is formulated into a fertilizer. In some instances, the composition is formulated into a slow-release fertilizer. In some instances, the composition is formulated into a specialty fertilizer. The processes disclosed herein can further include the step of mixing the condensate or one or more chemicals therein with another fertilizer, secondary nutrient, trace element, plant protection agent, filler, and/or with other fertilizer ingredients to form a mixed fertilizer.

Also disclosed are the following Embodiments 1 to 20 of the present invention. Embodiment 1 is a method for producing a urea condensation composition comprising: (a) reacting a solution comprising urea, formaldehyde, and at least one C2-C4 aldehyde under basic conditions to form a first composition; and (b) acidifying the first composition to form a urea condensation composition comprising at least one urea oligomer. Embodiment 2 is the method of Embodiment 1, wherein step (a) and (b) further comprises heat-treating the solution at a temperature of 25° C. to less than 100° C. Embodiment 3 is the method of any of Embodiments 1 to 2, wherein the at least one C2-C4 aldehyde comprises butyraldehyde, isobutyraldehyde, crotonaldehyde, or any combination thereof. Embodiment 4 is the method of any of Embodiments 1 to 3, wherein the urea condensation composition comprises a nitrogen content that is 100% water soluble. Embodiment 5 is the method of any of Embodiments 1 to 4, wherein the urea condensation composition comprises a nitrogen content that is at least 32%, 32% to 42%, or 35 to 38% by weight of the urea condensation composition. Embodiment 6 is the method of any of Embodiments 1 to 5, wherein the urea condensation composition comprises a water soluble nitrogen content comprising 60% or more, 75% or more, 80% or more, or 82% or more of cold water soluble nitrogen content. Embodiment 7 is the method of any one of Embodiments 1 to 6, wherein steps (a) and (b) comprise: (a) heating-treating the solution at a pH of about 8 to about 10 at a temperature of 40° C. to less than 100° C. for 30 minutes to 90 minutes, the solution comprising water, urea, formaldehyde, and isobutyraldehyde, wherein the mol. % ratio of formaldehyde to isobutyraldehyde is 9:1 to 1:3 and the mol. % ratio of urea to the combined formaldehyde and isobutyraldehyde is 2 or greater: 1; (b) acidifying the first composition from step (a) to have a pH of about 2 to about 5 to polymerize the urea in the presence of the formaldehyde and isobutyraldehyde at 25° C. to less than 60° C. for 30 minutes to 90 minutes, preferably at 45° C. for 60 minutes, to form a urea condensation composition comprising at least one methylene urea oligomer and at least one isobutylidenediurea derivative. Embodiment 8 is the method of any of Embodiments 1 to 7, further comprising: (c) formulating the urea condensation composition of step (b) in a fertilizer composition. Embodiment 9 is a urea condensation composition comprising: at least one C1-C4/urea oligomer; and less than 15 wt. % urea, wherein the urea condensation composition has a nitrogen content comprising 100% water soluble nitrogen content. Embodiment 10 is the urea condensation composition of Embodiment 9, wherein the water soluble nitrogen content comprises 75% or more, 80% or more, or 82% or more of cold water soluble nitrogen content. Embodiment 11 is the urea condensation composition of any of Embodiments 9 to 10, wherein the at least one C1-C4/urea oligomer comprises: at least two, three, or all four methylene urea oligomers selected from the group consisting of methylene diurea, dimethylene triurea, trimethylene tetraurea, and tetramethylene pentaurea; isobutylidenediurea; mono (ureidomethylene) isobutylenediurea; and bis(ureidomethylene) isobutylenediurea. Embodiment 12 is a method for producing a urea condensation composition comprising: (a) reacting a solution comprising urea and at least one first C1-C4 aldehyde or a derivative thereof under basic conditions to form a first composition; and (b) reacting the first composition and at least one second C1-C4 aldehyde or a derivative thereof under acidic conditions to form a urea condensation composition comprising at least one urea oligomer, wherein the at least one first C1-C4 aldehyde is different from the least one second C1-C4 aldehyde. Embodiment 13 is the method of Embodiment 12, wherein the at least one first C1-C4 aldehyde or at least one second C1-C4 aldehyde comprises formaldehyde, butyraldehyde, isobutyraldehyde, crotonaldehyde, or any combination thereof. Embodiment 14 is the method of Embodiment 12, wherein the first aldehyde in step (a) is formaldehyde and the second aldehyde in step (b) is a C2-C4 aldehyde. Embodiment 15 is the method of Embodiment 14, wherein the second C2-C4 aldehyde in step (b) is butyraldehyde, isobutyraldehyde, crotonaldehyde, or any combination thereof. Embodiment 16 is the method of any of Embodiments 12 to 15, wherein the urea condensation composition comprises a nitrogen content that is 100% water soluble. Embodiment 17 is the method of any of Embodiments 12 to 16, wherein the urea condensation composition comprises a nitrogen content that is at least 32%, 32% to 42%, or 34 to 38% by weight of the urea condensation composition. Embodiment 18 is the method of any of Embodiments 12 to 17, wherein the urea condensation composition comprises a water soluble nitrogen content comprising 60% or more, 75% or more, 80% or more, or 82% or more of cold water soluble nitrogen content. Embodiment 19 is the method of any of Embodiments 12 to 18, further comprising: (c) formulating the urea condensation composition of step (b) in a fertilizer composition.

The following includes definitions of various terms and phrases used throughout this specification.

"Free of hot water insoluble nitrogen (HWIN)" or "HWIN free" includes a composition that includes 0.5 wt. % or less of HWIN, preferably 0 wt. % HWIN.

A "C1-C4 aldehyde" and/or "C2-C4 aldehyde" can be a straight or branched aldehyde, saturated or unsaturated aldehyde, a substituted aldehyde, etc. having 1 to 4 carbon atoms or 2 to 4 carbon atoms, respectively. Non-limiting examples include formaldehyde, acetaldehyde, propionaldehyde, butyraldehyde, isobutyraldehyde, and crotonaldehyde.

"Nitrogen content" of a composition is the nitrogen contained in the composition. It can include free nitrogen in the composition and nitrogen present in a given compound (e.g., a C1-C4/urea oligomer of the present invention has nitrogen present in its chemical structure) that is present in the composition. The amount of nitrogen content in a composition can be expressed in a percentage of weight/weight (wt./wt.) of nitrogen in a composition. The nitrogen of the composition can be water soluble and/or hot-water insoluble.

"Water soluble-nitrogen" can include any nitrogen content that is soluble in water at or below 100° C. Water soluble-nitrogen content can include cold water-soluble nitrogen content (CWSN) and hot water-soluble nitrogen content (HWSN), but does not include hot water-insoluble nitrogen content (HWIN). "Cold water-soluble nitrogen" is any nitrogen containing compound that is soluble in water below and at 25° C. "Hot water-soluble nitrogen" is any nitrogen containing compound that is soluble in water below and at 100° C. but is not soluble in water below 26° C. "Hot water-insoluble nitrogen" is any nitrogen content that is not soluble in water below 101° C.

The term "short chain" methyleneureas can include methyleneureas containing one to five urea units.

The terms "about", "approximately", and "substantially" are defined as being close to, as understood by one of ordinary skill in the art. In one non-limiting instance, the terms are defined to be within 10%, preferably, within 5%, more preferably, within 1%, and most preferably, within 0.5%.

The terms "wt. %," "vol. %," or "mol. %" refers to a weight, volume, or molar percentage of a component, respectively, based on the total weight, the total volume, or the total moles of material that includes the component. In a non-limiting example, 10 grams of a component in 100 grams of the material that includes the component is 10 wt. % of component.

The use of the words "a" or "an" when used in conjunction with any of the terms "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification. With respect to the transitional phase "consisting essentially of" in one non-limiting aspect, a basic and novel characteristic of the process of the present invention is the ability to produce a urea condensation composition from urea, a first C1 to C4 aldehyde, and a second C1 to C4 aldehyde. Preferably, the composition is free of HWIN.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes, combinations, and modifications within the spirit and scope of the invention will become apparent to those skilled in the art from this detailed description.

BRIEF DESCRIPTION OF THE DRAWINGS

Advantages of the present invention may become apparent to those skilled in the art with the benefit of the following detailed description and upon reference to the accompanying drawings.

Figure 1:
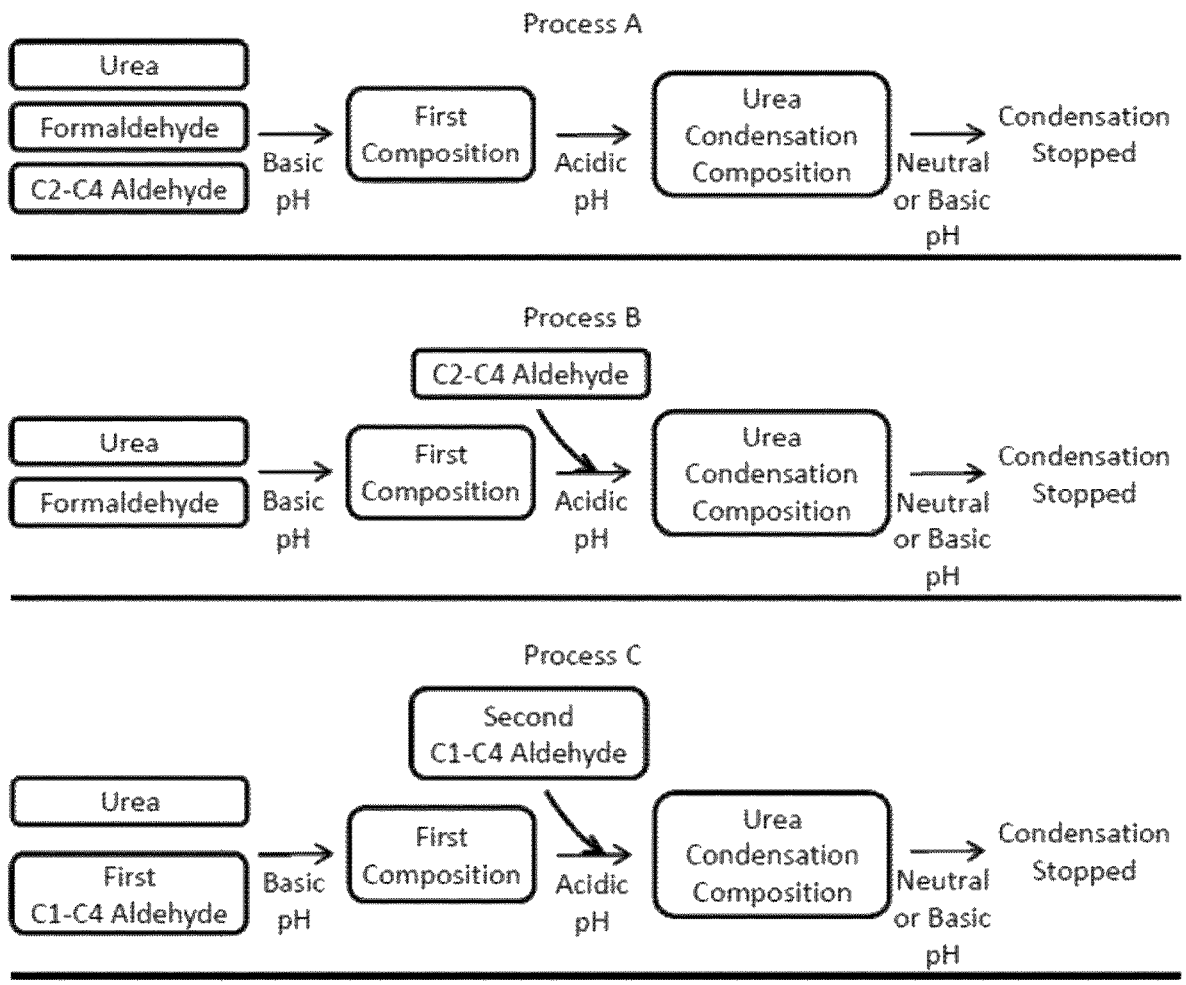
FIG. 1—is a representation of processes of the invention for producing urea-aldehyde condensates.

While the invention is susceptible to various modifications and alternative forms, specific embodiments thereof are shown by way of example in the drawings. The drawings may not be to scale.

DETAILED DESCRIPTION OF THE INVENTION

The processes of making urea-aldehyde condensation compositions of the present invention provide an elegant solution to the problem associated with controlling the degree of polymerization of urea-aldehyde condensation products. Notably, the present invention provides for processes that allow for the production of urea-aldehyde condensation products where the majority of the nitrogen content in the products is cold water-soluble nitrogen. Further, the products can be free of hot water-insoluble nitrogen (HWIN). Without wishing to be bound by theory, it is believed that the reaction conditions, order of reactions, and/or order of reactants used to make the urea-aldehyde condensation products of the present invention allow for more efficient control of the degree of polymerization during the condensation reaction, which is believed to result in HWIN-free urea-aldehyde condensates.

These and other non-limiting aspects of the present invention are discussed in further detail in the following sections with reference to the Figures.

A. Method of Making the Condensates

In particular embodiments, the process of the present invention provides efficient and controllable processes for the formation of a urea-aldehyde condensate. Urea, a first C1 to C4 aldehyde, and a second C1 to C4 aldehyde can be selectively converted to a urea-aldehyde condensate through or via a first basic reaction and a second acidification reaction. In a non-limiting aspect, the formed urea-aldehyde condensate can be further reacted in situ or separately to form further synthesis products (e.g., resin).

FIG. 1 provides an illustration of three processes of the present invention for producing urea-aldehyde condensates.

In one embodiment, the condensate can be generated by (a) reacting a solution containing urea, formaldehyde, and at least one C2-C4 aldehyde under basic conditions to form a first composition and (b) acidifying the first composition to form a urea condensation composition containing at least one urea oligomer (see FIG. 1, process A). In another embodiment, the condensate can be generated by (a) reacting a solution containing urea and formaldehyde under basic conditions to form a first composition, and (b) reacting the first composition and at least one C2-C4 aldehyde under acidic conditions to form a urea condensation composition containing at least one urea oligomer (see FIG. 1, process B). In yet another embodiment, the condensate can be generated by (a) reacting a solution containing urea and at least one first C1-C4 aldehyde or a derivative thereof under basic conditions to form a first composition, and (b) reacting the first composition and at least one second C1-C4 aldehyde or a derivative thereof under acidic conditions to form a urea condensation composition containing at least one urea oligomer, wherein the at least one first C1-C4 aldehyde is different from the least one second C1-C4 aldehyde (see FIG. 1, process C). In some instances, the reaction in step (a) is an addition reaction. In some instances, the reaction in step (b) is a condensation reaction. In some instances, the reactions are performed sufficiently to retain less than 25, 20, 15, 10, 5, 4, 3, 2, or 1 wt. % of urea in the urea condensation composition.

The solution containing urea can include a suitable solvent. Non-limiting examples of solvents include aqueous solvents and organic solvents. In some preferred instances, the solution is an aqueous solution. In some embodiments the solution contains urea in an amount from 20 to 90 wt %, from 40 to 85 wt %, from 50 to 80 wt % or from 50 to 85 wt %.

The temperature at which the reaction step (a) with urea is carried out is preferably below the boiling point of the aldehyde reacted in step (a) and water and is preferably below 100° C., more preferably at most 90° C., more preferably at most 80° C., for example at most 60° C., and/or at least 40° C., for example at least 50° C. Preferably, the temperature at which the reaction of the aldehyde reacted in step (a) with urea is carried out is in the range from 40 to 70° C. In some instances, the temperature of step (a) is 60° C.

The temperature at which the acidification step (b) is carried out is preferably below the boiling point of water and is preferably below 60° C., more preferably at most 55° C., more preferably at most 50° C., for example at most 45° C., and/or at least 25° C., for example at least 40° C. Preferably, the temperature at which the acidification step (b) is carried out is in the range from 25 to 60° C. In some instances, the temperature of step (b) is 45° C.

Preferably, the pressure for the process of the invention is atmospheric pressure (around 0.1 MPa).

B. Condensate Compositions

In some embodiments disclosed herein, a urea-aldehyde condensate is produced that is free of hot-water insoluble nitrogen (HWIN) content. In some instances, the majority of the urea-aldehyde condensate nitrogen content is cold water-soluble nitrogen (CWSN). In some instances, the urea condensation composition has a nitrogen content containing 100% water soluble nitrogen. The water-soluble nitrogen can be CWSN, hot water-soluble nitrogen (HWSN), or a combination of CWSN and HWSN. In some instances, the water soluble nitrogen contains 50% or more, 60% or more, 70% or more, 75% or more, 80% or more, or 82% or more of CWSN.

The urea-aldehyde condensate contains a C1-C4/urea oligomer. In some instances, the urea-aldehyde condensate contains a isobutylidenediurea derivative and at least one methylene urea oligomer. The urea-aldehyde condensate can include isobutylidenediurea, mono (ureidomethylene) isobutylenediurea, bis(ureidomethylene) isobutylenediurea, and at least two, three, or all four methylene urea oligomers selected from the group consisting of methylene diurea, dimethylene triurea, trimethylene tetraurea, and tetramethylene pentaurea. The urea-aldehyde condensate can contain a greater wt. % of methylene urea oligomers than isobutylidenediurea. The urea-aldehyde condensate can contain a greater wt. % of isobutylidenediurea than methylene urea oligomers. In some instances, the condensates contain less than 25, 20, 15, 10, 5, 4, 3, 2, or 1 wt. % urea.

C. Use of Condensate Compositions

The urea-aldehyde condensate(s) of the present invention can be used as, and/or combined with, a fertilizer. In some instances, the process of the invention can further include the step of mixing the urea-aldehyde condensate or the isolated urea-aldehyde condensate with another fertilizer, secondary nutrient, trace element, plant protection agent, filler, and/or with other fertilizer ingredients. In some instances the mixture forms a mixed fertilizer.

Examples of other fertilizers include, but are not limited to, nitrogen fertilizers, phosphate fertilizers, alkaline fertilizers, potassium and/or magnesium containing fertilizers, and/or manure, and/or secondary nutrients, and/or trace elements. Examples of nitrogen fertilizers include organic fertilizer containing nitrogen, such as methylene urea, crotonylidene diurea, oxamide, melamine, substituted triazones, ethylene diurea, triuret, and any mixtures of thereof. For example, the other fertilizers can additionally contain urea or nitrogen, potassium, phosphorus, and/or magnesium in the form of inorganic salts, or mixtures thereof. Easily soluble nitrogen components are, for example, ammonium nitrate, ammonium sulfate, or urea. Other salts that can be used are, for example, monoammonium phosphate, diammonium phosphate, potassium sulfate, potassium chloride, magnesium sulphate, calcium superphosphate, disodium hydrogen phosphate, ferric chloride, manganous chloride, calcium chloride, magnesium phosphate, ammonia, and potassium oxide. The other fertilizers can contain single-nutrient, multi-nutrient, and other possible fertilizer ingredients, for example, which contain nutrients such as nitrogen, potassium, or phosphorus, individually or in combination. In some instances, the nutrients are in the form of their salts. Examples of these are nitrogen and phosphorous fertilizers (NP), nitrogen and potassium fertilizers (NK), potassium and phosphorous fertilizers (PK), and nitrogen, phosphorus, and potassium fertilizers (NPK), lime nitrate of ammonium, ammonia sulfate, ammonia sulfa-nitrate, and urea.

Examples of secondary nutrients include, but are not limited to, Ca, S, and B. Trace elements, for example selected from among Fe, Mn, Cu, Zn, Mo, or mixtures thereof, can also be present for example in the form of inorganic salts. The amounts of secondary nutrients or trace elements in the mixed fertilizer can, for example, be chosen in the range from 0.5 to 5 wt. %, based upon the total weight of the mixed fertilizer.

Examples of plant protection agents include but are not limited to insecticides, fungicides, growth regulators, nitrification inhibitors, and any mixtures of them. Examples of fillers include but are not limited to clay, peat, etc. Examples of other fertilizer ingredients are for example described in Ullmann's Encyclopedia of Industrial Chemistry, $5^{th}$ edition, 1987, Volume A10, pages 363 to 401, DE-A-41 28 828, DE-A-19 05 834, or DE-A-196 31 764, which references are hereby incorporated by reference.

EXAMPLES

The present invention will be described in greater detail by way of specific examples. The following examples are offered for illustrative purposes only, and are not intended to limit the invention in any manner. Those of skill in the art will readily recognize a variety of noncritical parameters, which can be changed or modified to yield essentially the same results.

Example 1

Process A: Synthesis of a Urea-Aldehyde Condensate Using Formaldehyde and Isobutyraldehyde in a First Step Under Basic Conditions Described below are non-limiting examples of one pot production of urea-aldehyde condensates. The aldehydes used were formaldehyde (FA) and isobutyraldehyde (IBA), wherein the ratio of FA to IBA ranged from 90/10 to 25/75. The synthesis of MU-IBDU involved a two-step process. The first step involved reacting a solution of urea (2 eq) in water with known ratios of FA/IBA (1 eq) under basic pH (~8-9) at 60° C. for 1 hr. The pH in the first step was adjusted with 10% KOH solution. The second step involved acidification to a pH ~3-4 to initiate a polymerization reaction. The pH in the second step was adjusted with 10% $H_3PO_4$. The mixture was heated at 45° C. for 1 hr and finally quenched by neutralizing. The product could be produced as, or processed as, a powder. As an example, a yield of 63 grams of a MU-IBDU solid was produced when 60 g urea (2 eq) in 180 ml water was reacted with 1 eq 75/25 FA/IBA (30.5 ml, 0.75 eq FA followed by 11.4 ml, 0.25 eq IBA).

Example 2

Characterization of Urea-Aldehyde Condensates of Example 1

The condensates produced using the reactions outlined in Example 1 were characterized using high performance liquid chromatography (HPLC) with a photodiode array (PDA) detector. By varying the ratios of FA/IBA, different ratios of MU-IBDU derivatives were obtained with different nitrogen (N) content (35-39%). The condensates contained no hot water-insoluble nitrogen (HWIN) and the MU-IBDU derivatives consists majorly of short chain MU products along with IBDU derivatives. The reaction product retained 15% or less of unreacted urea. The MU-IBDU derivatives are expected to work well as a fertilizer composition in all seasons with a steady release of nitrogen.

Methods for HPLC Analysis:

Depending on the factors like solubility and stability of MU and IBDU, two individual HPLC methods have been developed for the qualitative analysis of methylene urea oligomers and IBDU in MU-IBDU composition.

Method 1—Determination of MU Oligomers:

The analysis of methylene urea oligomers was carried out using a Shimadzu HPLC. 50 mg of the MU-IBDU sample was dissolved in 10 ml of water and heated at 60° C. for 30 mins, filtered and analyzed using following HPLC conditions: Chromatography column: Synergi, 4 μm, Hydro-RP, 250×4.6 mm; Column oven temp.: 60° C.; Mobile phase-100% Milli Q water; Injection volume: 5 μL; Run time: 30 mins; Wavelength Monitored: 195 nm. The peaks of methylene urea oligomers were assigned based on liquid chromatography/mass spectrometry (LCMS) results.

Method 2—Determination of IBDU:

The analysis of IBDU was carried out using a Shimadzu HPLC. Calibration standards of IBDU were prepared by dissolving the IBDU standard in acetonitrile:Milli Q water (80:20% v/v) by sonication for 30 mins. About 50 mg of the sample was dissolved in acetonitrile:Milli Q water (80:20% v/v) by sonicating the samples for about 30 mins. Samples were filtered and analyzed using the following HPLC conditions: Chromatography column: Synergi, 4 μm, Hydro-RP, 250×4.6 mm; Column oven temp.: 25° C.; Mobile phase-Milli Q water:acetonitrile (95:5) Isocratic condition; Injection volume: 5 μL; Run time: 30 mins; Wavelength Monitored: 195 nm. The calibration curve was found to be linear over the concentration range of 0.1 to 1.00 mg/mL with $r^2=0.9999$. The peaks of IBDU were assigned based on LCMS results.

Figure 2A:
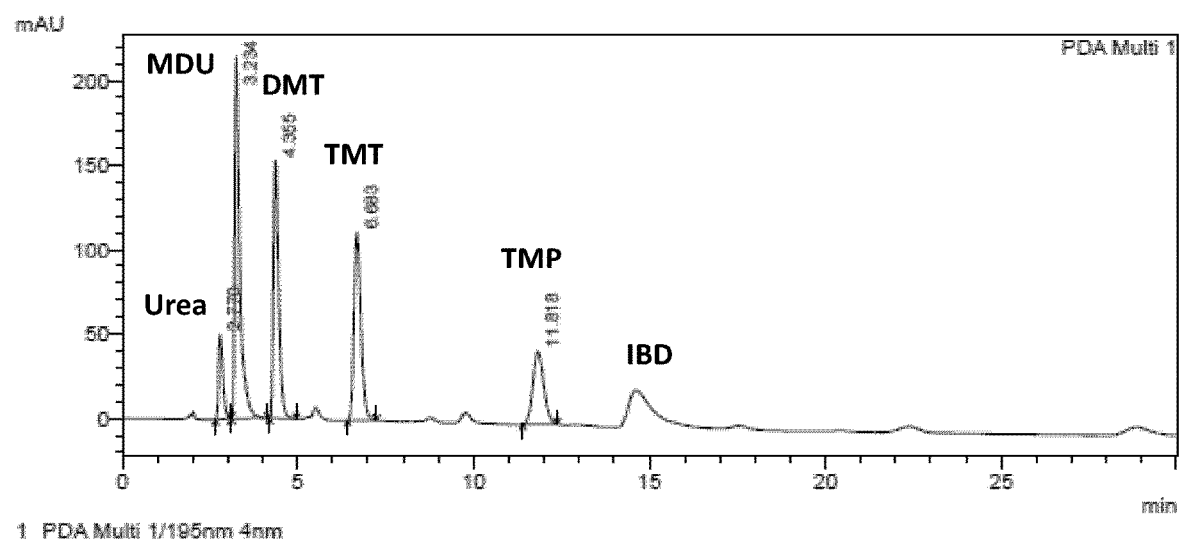
FIGS. 2A and 2B—(A) is a representative HPLC chromatogram of methylene urea (MU) oligomers. (B) is the raw tabulated results from the representative chromatogram. MDU is monomethylenediurea; DMTU is dimethylenetriurea; TMTU is trimethylenetetraurea; TMPU is tetramethylenepentaurea.
Figure 2B:
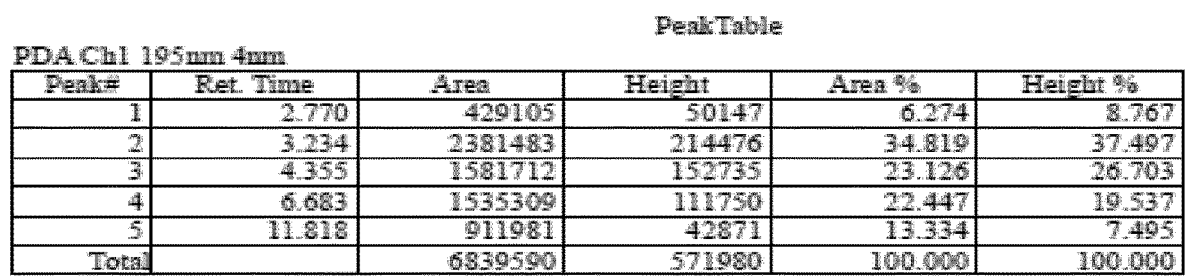

Results of HPLC Analysis of Methylene Urea (MU) Oligomers by Process A:

A representative chromatogram following the above protocol is shown in FIG. 2A and raw tabulated results in FIG. 2B. The ratios of MU oligomers in different MU-IBDU products as determined by HPLC are show in Table 1. The MU fraction mostly consisted of a mixture of unreacted urea, Methylene diurea (MDU), Dimethylene triurea (DMTU), Trimethylene tetraurea (TMTU) and Tetramethylene pentaurea (TMPU).

TABLE 1

| Sample (ratio of FA/IBA reactants) | Urea (%) | MDU (%) | DMTU (%) | TMTU (%) | TMPU (%) |
|---|---|---|---|---|---|
| MU-IBDU (90/10) | 5.544 | 27.643 | 20.538 | 29.763 | 16.512 |
| MU-IBDU (85/15) | 6.164 | 34.040 | 23.694 | 23.809 | 12.296 |
| MU-IBDU (75/25) | 6.274 | 34.819 | 23.126 | 22.447 | 13.334 |
| MU-IBDU (50/50) | 8.193 | 52.037 | 13.315 | 15.247 | 11.181 |
| MU-IBDU(25/75) | 15.306 | 54.136 | 23.795 | 6.763 | — |

The above results clearly show that the degree of polymerization decreases with an increase in IBA concentration. IBDU is found to undergo hydrolysis under the above sample preparation condition (60° C.) and hence not quantified.

Figure 3:
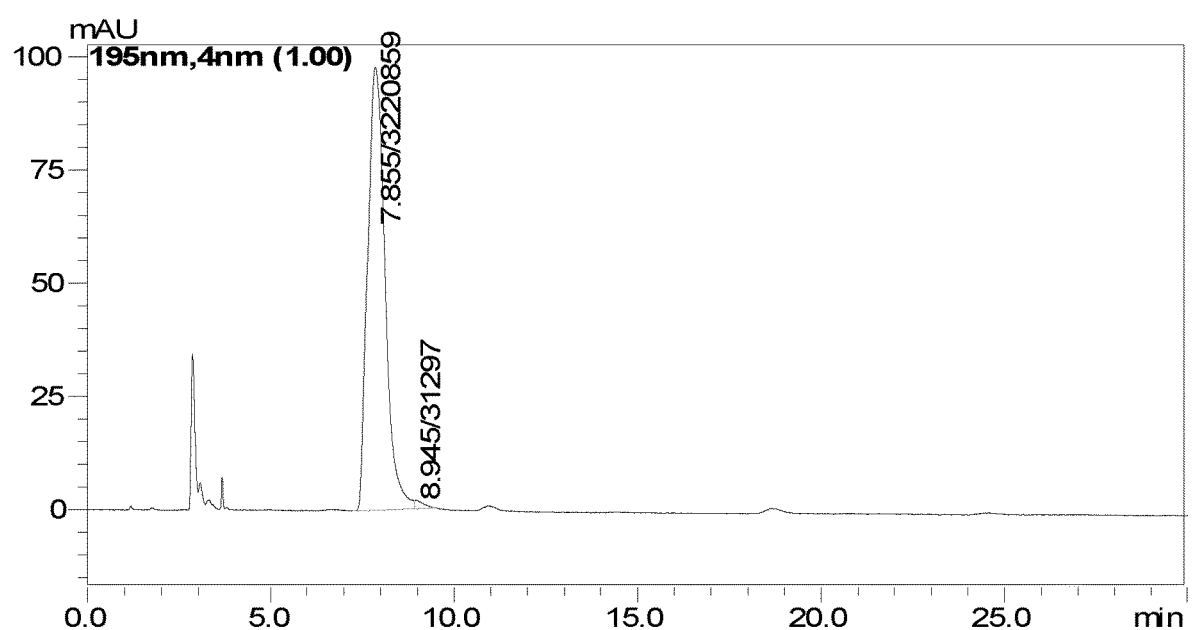
FIG. 3—is a representative HPLC chromatogram for IBDU.
Figure 4:
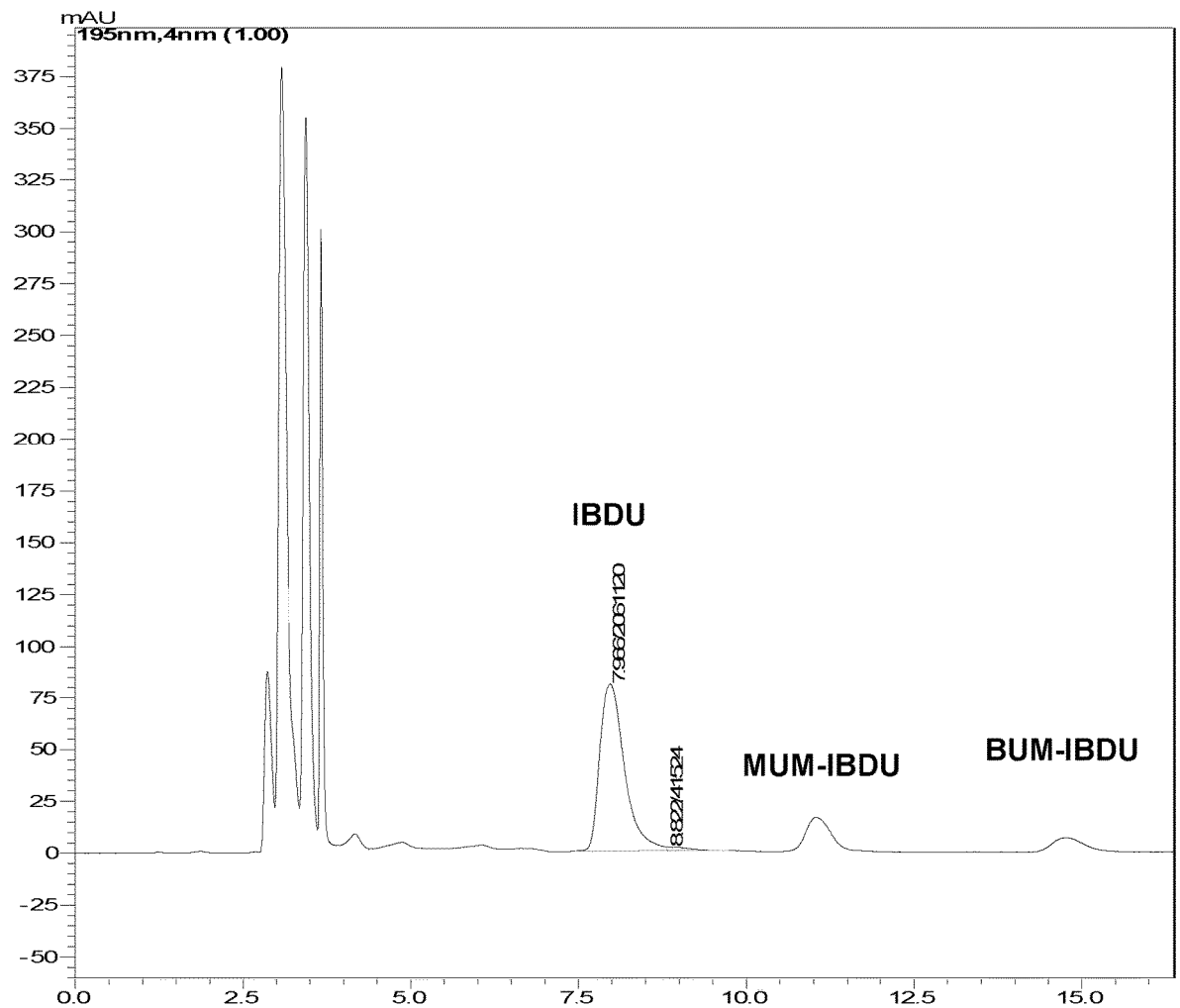
FIG. 4—is a representative HPLC chromatogram of MU-IBDU derivatives. MUM-IBDU is mono (ureidomethylene) isobutylenediurea; BUM-IBDU is bis (ureidomethylene) isobutylenediurea.

Results of HPLC Analysis of IBDU Content by Process A:

A representative chromatogram for IBDU following the protocol above is shown in FIG. 3. A representative chromatogram of MU-IBDU derivatives is shown in FIG. 3. The IBDU content in different MU-IBDU products were determined by HPLC and the results are shown in Table 2. The IBDU fraction consisted mainly of IBDU and IBDU derivatives such as mono (ureidomethylene) isobutylenediurea (MUM-IBDU) and bis(ureidomethylene) isobutylenediurea (BUM-IBDU).

TABLE 2

| Sample (ratio of FA/IBA reactants) | IBDU wt % |
|---|---|
| MU-IBDU (90/10) | 9.063% |
| MU-IBDU (75/25) | 27.1% |
| MU-IBDU (50/50) | 55.09% |

Example 3

Properties of Urea-Aldehyde Condensates of Example 1

The total Nitrogen (N) content of the condensate of Example 1 was determined using an Elemental analyzer, Vario EL cube. The CWSN of the condensate was determined using AOAC methods 945.01. Briefly, the MU-IBDU product (1 g) was extracted in water (250 ml) at room temperature for 15 minutes and filtered. The N content of the residue was determined. The HWSN of the condensate was determined using AOAC method 955.05. Briefly, the cold water insoluble fraction was extracted with phosphate buffer at 100° C. for 30 minutes and filtered. No HWIN residue was found upon filtration. The results are shown in Table 3.

TABLE 3

| Sample (ratio of FA/IBA reactants) | Total N content (%) | CWSN (%) | HWSN (%) | HWIN (%) |
|---|---|---|---|---|
| MU-IBDU (90/10) | 39.2 | 82 | 18 | 0 |
| MU-IBDU (75/25) | 37.4 | 86.5 | 13.5 | 0 |
| MU-IBDU (50/50) | 36.8 | 87 | 13 | 0 |
| MU-IBDU 25/75) | 36.2 | 86.2 | 13.8 | 0 |

The results clearly show that the composition obtained by these processes have resulted in compositions free of hot water-insoluble nitrogen (HWIN). The cold water-soluble nitrogen (CWSN) is found to be the major fraction (>80%) along with <20% hot water-soluble nitrogen (HWSN). It has also been observed that IBA helps in controlling the degree of polymerization and thereby increases the CWSN content.

Example 4

Process B: Synthesis of a Urea-Aldehyde Condensate Using Formaldehyde in a First Step Under Basic Conditions and a C2-C4 Aldehyde in a Second Step Under Acidic Conditions Described below are non-limiting examples of one pot synthesis of urea-aldehyde condensates. The aldehydes used were formaldehyde (FA) and isobutyraldehyde (IBA), wherein the ratio of FA to IBA ranged from 90/10 to 25/75. The synthesis of MU-IBDU involved a two-step process. The first step involved reacting a solution of urea (2 equivalents) in water with known ratios of FA under basic pH (~8-9) at 60° C. for 1 hr. The pH in the first step was adjusted with 10% KOH solution. The second step involved addition of known ratio of IBA followed by acidification to a pH ~3-4 to initiate a polymerization reaction. The pH in the second step was adjusted with 10% $H_3PO_4$. The mixture was heated at 45° C. for 1 hour and finally quenched by neutralizing. The product could be produced as, or processed as, a powder. As an example, a yield of 10.5 grams of a MU-IBDU solid was produced when 10 g urea (2 equivalents) in 20 ml water was reacted with 1 equivalent 75/25 FA/IBA (5.08 ml, 0.75 equivalent FA in first step and 1.9 ml, 0.25 equivalent IBA in second step).

Example 5

Characterization of Urea-Aldehyde Condensates of Example 4

The condensates produced using the reactions outlined in Example 4 were characterized using high performance liquid chromatography (HPLC) with a photodiode array (PDA) detector as described above in Example 2, method 1 and method 2. By varying the ratios of FA/IBA, different ratios of MU-IBDU derivatives were obtained with different nitrogen (N) content (34-38%). The condensates contained no hot water-insoluble nitrogen (HWIN) and the MU-IBDU derivatives consists majorly of short chain MU products. The reaction product retained 18% or less of unreacted urea. The MU-IBDU derivatives are expected to work well as a fertilizer composition in all seasons with a steady release of nitrogen.

Results of HPLC Analysis of Methylene Urea (MU) Oligomers by Process B:

The ratios of MU oligomers in different MU-IBDU products, as determined by HPLC for process B, are show in Table 4. The MU fraction mostly consisted of a mixture of unreacted urea, Methylene diurea (MDU), Dimethylene triurea (DMTU), Trimethylene tetraurea (TMTU) and Tetramethylene pentaurea (TMPU).

TABLE 4

| Sample (ratio of FA/IBA reactants) | Urea (%) | MDU (%) | DMTU (%) | TMTU (%) | TMPU (%) |
|---|---|---|---|---|---|
| MU-IBDU (75/25) | 4.714 | 23.583 | 14.909 | 27.049 | 19.270 |
| MU-IBDU (50/50) | 9.77 | 47.613 | 24.565 | 12.42 | 5.62 |
| MU-IBDU (25/75) | 18.2 | 61.689 | 15.2689 | 4.803 | — |

Example 6

Properties of Urea-Aldehyde Condensates of Example 4

The total Nitrogen (N) content of the condensate of Example 4 was determined using an Elemental analyzer, Vario EL cube. The CWSN and HWSN of the condensate was determined using AOAC methods 945.01 and 955.05, as described above in Example 3. After solubilizing the CWSN and HWSN, no HWIN residue was found upon filtration. The results are shown in Table 5.

TABLE 5

| Sample (ratio of FA/IBA reactants) | Total N content (%) | CWSN (%) | HWSN (%) | HWIN (%) |
|---|---|---|---|---|
| MU-IBDU (75/25) | 37.5 | 67.58 | 32.42 | 0 |
| MU-IBDU (50/50) | 36.5 | 96 | 3.45 | 0 |
| MU-IBDU (25/75) | 34.0 | 85 | 14.99 | 0 |

The results clearly show that the composition obtained by these processes have resulted in compositions free of hot water-insoluble nitrogen (HWIN). The cold water-soluble nitrogen (CWSN) is found to be the major fraction (>65%) along with <35% hot water-soluble nitrogen (HWSN). It has also been observed that IBA helps in controlling the degree of polymerization and thereby increases the CWSN content.

The invention claimed is:
1. A urea condensation composition comprising:
   isobutylidenediurea;
   mono (ureidomethylene) isobutylenediurea;
   bis(ureidomethylene) isobutylenediurea;
   at least two, three, or all four methylene urea oligomers selected from the group consisting of methylene diurea, dimethylene triurea, trimethylene tetraurea, and tetramethylene pentaurea; and
   less than 15 wt. % urea,
   wherein the urea condensation composition has a nitrogen content comprising 100% water soluble nitrogen content.
2. The urea condensation composition of claim 1, wherein the water soluble nitrogen content comprises 75% or more of cold water soluble nitrogen content.
3. The urea condensation composition of claim 1, comprising a nitrogen content that is at least 32% by weight of the urea condensation composition.
4. The urea condensation composition of claim 1, comprising a water soluble nitrogen content comprising 60% or more of cold water soluble nitrogen content.
5. The urea condensation composition of claim 1, comprising a nitrogen content that is 32% to 42% by weight of the urea condensation composition.
6. The urea condensation composition of claim 1, comprising a nitrogen content that is 35 to 38% by weight of the urea condensation composition.
7. The urea condensation composition of claim 1, comprising a water soluble nitrogen content comprising 80% or more of cold water soluble nitrogen content.
8. The urea condensation composition of claim 1, comprising a water soluble nitrogen content comprising 82% or more of cold water soluble nitrogen content.
9. A method for producing the urea condensation composition of claim 1, the method comprising:
   (a) reacting a solution comprising urea, formaldehyde, and at least one C2-C4 aldehyde under basic conditions to form a first composition; and
   (b) acidifying the first composition to form the urea condensation composition.
10. A method for producing the urea condensation composition of claim 1, the method comprising:
   (a) reacting a solution comprising urea and at least one first C1-C4 aldehyde or a derivative thereof under basic conditions to form a first composition; and
   (b) reacting the first composition and at least one second C1-C4 aldehyde or a derivative thereof under acidic conditions to form the urea condensation composition, wherein the at least one first C1-C4 aldehyde is different from the least one second C1-C4 aldehyde.

* * * * *